(12) United States Patent
Barkóczy et al.

(10) Patent No.: US 6,930,110 B2
(45) Date of Patent: Aug. 16, 2005

(54) SUBSTITUTED ALKYLAMINOPYRIDAZINONE DERIVATIVES, PROCESS FOR THE PREPARATION THEREOF AND PHARMACEUTICAL COMPOSITION CONTAINING THE SAME

(75) Inventors: József Barkóczy, Budapest (HU); András Egyed, Budapest (HU); István Gacsályi, Budapest (HU); László Hársing, Budapest (HU); Hajnalka Kompagne, Budapest (HU); Péter Kótay Nagy, Vác (HU); György Lévay, Budakeszi (HU); Csilla Leveleki, Budapest (HU); Bernadett Martonné Markó, Budapest (HU); Anikó Miklósné Kovács, Budapest (HU); Éva Schmidt, Budapest (HU); Gyula Simig, Budapest (HU); Gábor Szénási, Budapest (HU); János Wellmann, Budapest (HU)

(73) Assignee: Egis Gyogyszergyar Rt., Budapest (HU)

( * ) Notice: Subject to any disclaimer, the term of this patent is extended or adjusted under 35 U.S.C. 154(b) by 0 days.

(21) Appl. No.: 10/491,151

(22) PCT Filed: Sep. 26, 2002

(86) PCT No.: PCT/HU02/00096

§ 371 (c)(1),
(2), (4) Date: Jun. 28, 2004

(87) PCT Pub. No.: WO03/027097

PCT Pub. Date: Apr. 3, 2003

(65) Prior Publication Data

US 2004/0242873 A1 Dec. 2, 2004

(30) Foreign Application Priority Data

Sep. 27, 2001 (HU) .............................. 0103912

(51) Int. Cl.$^7$ .................... A61K 31/501; C07D 405/14; C07D 405/12
(52) U.S. Cl. .................................. 514/252.01; 544/238
(58) Field of Search ...................... 544/238; 514/252.01

(56) References Cited

U.S. PATENT DOCUMENTS 3,931,176 A    1/1976   Houlihan

FOREIGN PATENT DOCUMENTS

| EP | 0 372 305 A | 6/1990 |
|---|---|---|
| PL | 164 079 B | 6/1994 |
| WO | WO 96 38441 A | 12/1996 |
| WO | WO 99 64402 A | 12/1996 |

*Primary Examiner*—Bernard Dentz
(74) *Attorney, Agent, or Firm*—Birch, Stewart, Kolasch & Birch, LLP

(57) ABSTRACT

The invention relates to substituted alkylaminopyridazinone derivatives of the general Formula (I), (wherein $R_1$ is hydrogen or alkyl having 1–4 carbon atoms; one of X and Y stands for hydrogen or halogen and the other represents a group of the general Formula (II), $R_2$ is hydrogen or alkyl having 1–4 carbon atoms; n is 1, 2 or 3; $R_3$ stands for hydrogen, alkyl having 1–4 carbon atoms or aryl-($C_{1-4}$ alkyl); Z stands for oxygen; or $R_3$ and Z together with the groups placed between them form a piperazine ring; and $R_4$ stands for hydrogen, halogen, trifluoromethyl or alkoxy having 1–4 carbon atoms) and pharmaceutically acceptable acid addition salts thereof. The invention compounds are useful in the treatment of anxiolytic conditions and cognitive disorders.

20 Claims, 1 Drawing Sheet

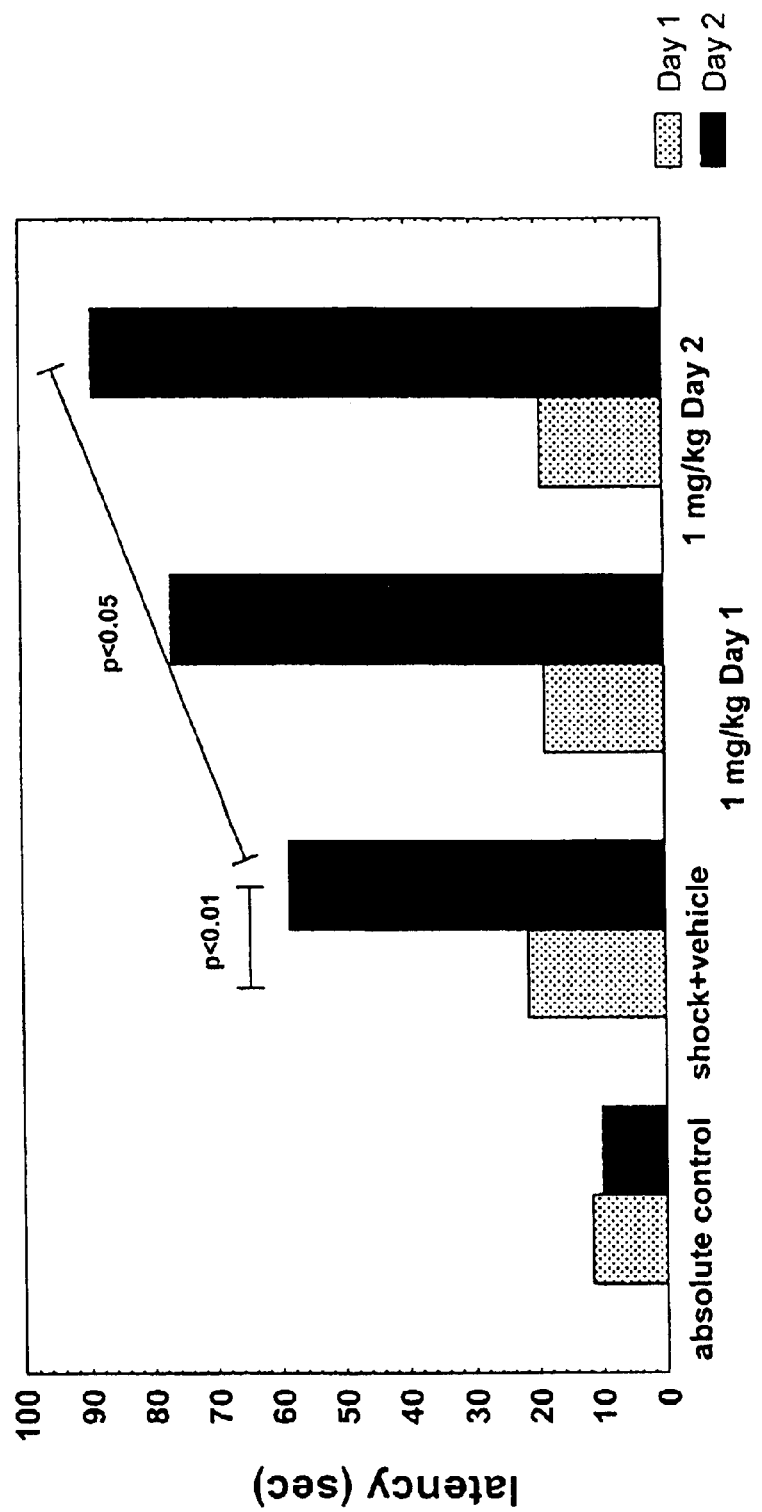

SUBSTITUTED ALKYLAMINOPYRIDAZINONE DERIVATIVES, PROCESS FOR THE PREPARATION THEREOF AND PHARMACEUTICAL COMPOSITION CONTAINING THE SAME

This application is a 371 of PCT/HU02/00096 filed Sep. 26, 2002.

FIELD OF THE INVENTION

The invention relates to new substituted alkylaminopyridazinone derivatives, process for the preparation thereof and pharmaceutical compositions containing the same.

BACKGROUND OF THE INVENTION

The present invention relates to the use of compounds of general Formula I for the treatment of different forms of anxiety.

Anxiety is a major CNS symptom accompanied by many psychiatric disorders, medical and surgical conditions and stress situations. Benzodiazepines such as diazepam, chlordiazepoxide, and alprazolam etc. are the most commonly used agents in the various anxiety disorders. However, sedative and amnestic side effects are a major disadvantage of these drugs especially in disorders affecting active, working populations. Moreover, withdrawal symptoms may occur following suspension of benzodiazepine administration after long term therapy. Therefore, finding of an effective anxiolytic/antistress compound without such undesirable side effects, low addictive potential and good safety features still remains one of the most challenging aims of CNS pharmacology research these days.

Piperazinylalkylamino-3(2H)-pyridazinone derivatives having blood pressure lowering effect and being suitable for the treatment of heart failure and peripheral circulatory disturbances are known from EP-A No. 372 305.

SUMMARY OF THE INVENTION

The object of the present invention is to provide new anxiolytic active ingredients free of antihypertensive properties.

The above object is achieved by the present invention.

The present invention is directed to new compounds of the general Formula

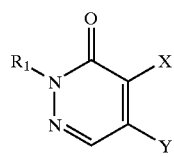
(I)

(wherein
$R_1$ is hydrogen or alkyl having 1–4 carbon atoms;
one of X and Y stands for hydrogen or halogen and the other represents a group of the general Formula

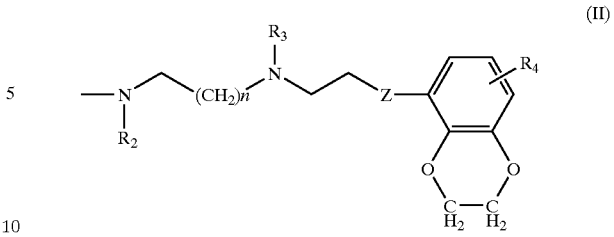
(II)

$R_2$ is hydrogen or all having 1–4 carbon atoms;
n is 1, 2 or 3;
$R_3$ stands for hydrogen, alkyl having 1–4 carbon atoms or aryl-($C_{1-4}$ alkyl);
Z stands for oxygen; or
$R_3$ and Z together with the groups placed between them form a piperazine ring; and
$R_4$ stands for hydrogen, halogen, trifluoromethyl or alkoxy having 1–4 carbon atoms)

and pharmaceutically acceptable acid addition salts thereof.

According to a further feature of the present invention there is provided a process for the preparation of compounds of the general Formula I (wherein $R_1$ is hydrogen or alkyl having 1–4 carbon atoms;
one of X and Y stands for hydrogen or halogen and the other represents a group of the general Formula II;
$R_2$ is hydrogen or alkyl having 1–4 carbon atoms;
n is 1, 2 or 3;
$R_3$ stands for hydrogen, alkyl having 1–4 carbon atoms or aryl-($C_{1-4}$ alkyl);
Z stands for oxygen; or
$R_3$ and Z together with the groups placed between them form a piperazine ring; and
$R_4$ stands for hydrogen, halogen, trifluoromethyl or alkoxy having 1–4 carbon atoms)

and pharmaceutically acceptable acid addition salts thereof which comprises a) for the preparation of compounds of the general Formula I, (wherein X represents hydrogen or halogen, Y stands for a group of the general Formula II and $R_2$, $R_3$, $R_4$, Z and n are as stated above) reacting a compound of the general Formula

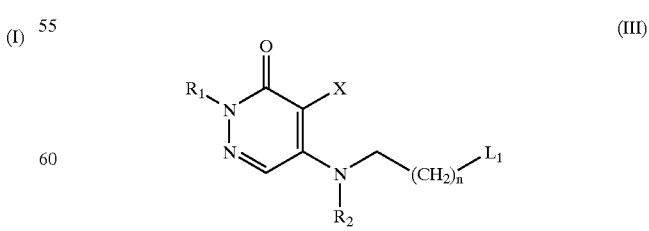
(III)

(wherein $L_1$ represents a leaving group, and $R_1$, $R_2$, X and n are as stated above) with an amine of the general Formula

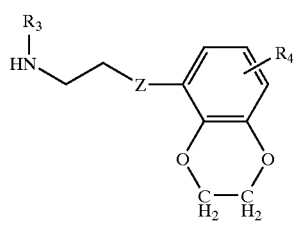
(IV)

(wherein $R_3$, $R_4$ and Z are as stated above); or b) for the preparation of compounds of the general Formula I, (wherein Y represents hydrogen or halogen, X stands for a group of the general Formula II and $R_2$, $R_3$, $R_4$, Z and n are as stated above), reacting a compound of the general Formula

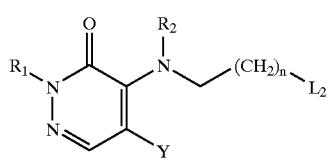
(V)

(wherein $L_2$ is a leaving group, and $R_1$, $R_2$, Y and n are as stated above) with an amine of the general Formula IV (wherein $R_3$, $R_4$ and Z are as stated above); or c) for the preparation of compounds of the general Formula I, (wherein X represents hydrogen or halogen, Y stands for a group of the general Formula II and $R_2$, $R_3$, $R_4$, Z and n are as stated above, with the proviso that $R_3$ together with Z and the groups between them is other than a piperazine ring), reacting a compound of the general Formula

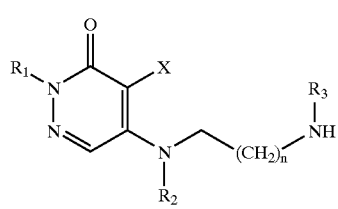
(VI)

(wherein $R_1$, $R_2$, $R_3$, X and n are as stated above) with a compound of the general Formula

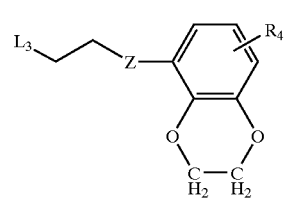
(VII)

(wherein $R_4$ and Z are as stated above and $L_3$ stands for a leaving group); or d) for the preparation of compounds of the general Formula I, (wherein Y stands for hydrogen or halogen, X stands for a group of the general Formula II and $R_2$, $R_3$, $R_4$, Z and n are as stated above with the proviso that $R_3$ together with Z and the groups between them is other than a piperazine ring), reacting a compound of the general Formula

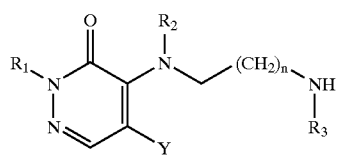
(VIII)

(wherein $R_1$, $R_2$, $R_3$, Y and n are as stated above) with a compound of the general Formula VII (wherein Z and $R_4$ are as stated above and $L_3$ stands for a leaving group); or e) for the preparation of compounds of the general Formula I, (wherein X represents halogen and Y stands for a group of the general Formula II and/or Y represents halogen and X stands for a group of the general Formula II and $R_1$, $R_2$, $R_3$, $R_4$, Z and n are as stated above), reacting a dihalopyridazinone derivative of the general Formula

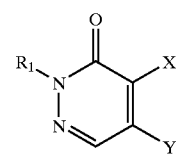
(IX)

(wherein $R_1$ is as stated above and X and Y independently from each other stand for halogen) with a compound of the general Formula

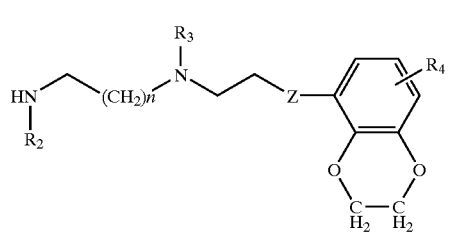
(X)

(wherein $R_2$, $R_3$, $R_4$, Z and n are as stated above),
and, if desired, subjecting an obtained substituted alkylaminopyridazinone derivative of the general Formula I (wherein X or Y stand for halogen) to catalytic dehalogenation to obtain a substituted alkylaminopyridazinone derivative of the general Formula I or its hydrochloride salt, wherein X represents hydrogen and Y stands for a group of the general Formula II or X represents a group of the general Formula II and Y stands for hydrogen; and/or converting an obtained compound of the general Formula I into a pharmaceutically acceptable acid addition salt thereof or liberating a compound of the general Formula I from an acid addition salt thereof.

According to a still further feature of the present invention there are provided pharmaceutical compositions comprising as active ingredient at least one compound of the general Formula I or a pharmaceutically acceptable acid addition salt thereof in admixture with suitable inert pharmaceutical carriers and/or auxiliary agents.

According to a still further feature of the present invention there is provided a process for the preparation of pharmaceutical compositions which comprises admixing at least one compound of the general Formula I or a pharmaceutically acceptable acid addition salt thereof with suitable inert pharmaceutical carriers and/or auxiliary agents.

According to a still further feature of the present invention there is provided the use of compounds of the general Formula I or pharmaceutically acceptable acid addition salts thereof as pharmaceutical active ingredients.

According to a still further feature of the present invention there is provided a method of treatment of anxiolytic conditions and cognitive disorders which comprises administering to the person in need of such treatment a pharmaceutically effective amount of a compound of the general Formula I or a pharmaceutically acceptable acid addition salt thereof.

DESCRIPTION OF THE PREFERRED EMBODIMENT

The definition of the term used in the description and the claims is as follows:

The term "halogen" is fluorine, chlorine, bromine and iodine, preferably chlorine.

The term "alkyl having 1–4 carbon atoms" relates to straight or branched chain alkyl groups, preferably methyl, ethyl, isopropyl, n-propyl, n-butyl, sec.-butyl, isobutyl or tert.-butyl.

The term "alkoxy having 1–4 carbon atoms" relates to straight or branched chain alkoxy groups, preferably methoxy, ethoxy, isopropoxy or n-butoxy, preferably methoxy.

The term "aryl-($C_{1-4}$ alkyl)" is e.g. benzyl, β-phenyl-ethyl etc., preferably benzyl.

The term "leaving group" relates to halogen (e.g. chlorine, bromine) or alkylsulfonyloxy groups (e.g. methylsulfonyloxy) or arylsulfonyloxy groups (e.g. benzylsulfonyloxy, p-toluene-sulfonyloxy).

The term "pharmaceutically acceptable acid addition salts of the substituted alkylaminopyridazinone derivatives of the Formula I" relates to the non-toxic acid addition salts of the compounds formed with inorganic acids such as hydrochloric acid, hydrobromic acid, sulfuric acid, phosphoric acid etc. or organic acids such as formic acid, acetic acid, maleic acid, fumaric acid, lactic acid, tartaric acid, succinic acid, citric acid, benzenesulfonic acid, p-toluenesulfonic acid, methanesulfonic acid etc.

The following compounds form a preferred sub-group of the invention compounds, namely compounds of the general Formula I
(wherein
$R_1$ is hydrogen or methyl;
one of X and Y stands for hydrogen or chlorine and the other represents a group of the general Formula II;
$R_2$ is hydrogen or methyl;
n is 1, 2 or 3;
$R_3$ stands for hydrogen;
Z stands for oxygen; or
$R_3$ and Z together with the groups placed between them form a piperazine ring; and
$R_4$ stands for hydrogen or chlorine)
and pharmaceutically acceptable acid addition salts thereof.

The following compounds of the general Formula I and pharmaceutically acceptable acid addition salts possess particularly useful pharmaceutical properties:

5-chloro-4-{4-[4-(2,3-dihydrobenzo[1,4]dioxine-5-yl)-piperazine-1-yl]-butylamino}-2H-piridazine-3-one;
4-chloro-5-{2-[4-(2,3-dihydro-1,4-benzodioxine-5-yl)-piperazine-1-yl]-ethylamino}-2-methyl-2H-piridazine-3-one and its monohydrate;
4-chloro-5-{2-[4-(2,3-dihydrobenzo[1,4]dioxine-5-yl)-piperazine-1-yl]ethyl}methylamino-2H-pyridazine-3-one;
4-{3-[2-(2,3-dihydrobenzo[1,4]dioxine-5-yloxy)ethylamino]-propylamino}-2H-pyridazine-3-one;
5-{2-[4-(2,3-dihydro-1,4-benzodioxine-5-yl)-piperazine-1-yl]-ethylamino}-2H-pyridazine-3-one;
5-{2-[4-(7-chloro-2,3-dihydrobenzo[1,4]dioxine-5-yl)-piperazine-1-yl]ethylamino}-2H-pyridazine-3-one;
5-{3-[4-(2,3-dihydro-1,4-benzodioxine-5-yl)piperazine-1-yl]-propylamino}-2H-pyridazine-3-one;
5-{2-[2-(2,3-dihydrobenzo[1,4]dioxine-5-yloxy)ethylamino)-ethylamino)-2H-pyridazine-3-one;
5-{2-[4-(2,3-dihydro1,4-benzodioxine-5-yl)-piperazine-1-yl]-ethylamino}-2-methyl-2H-pyridazine-3-one;
5-({2-[4-(2,3-dihydro-benzo[1,4]dioxine-5-yl)-piperazine-1-yl]-ethyl}-methyl-amino)-2H-pyridazine-3-one;
5-(2-(4-(2,3-dihydro-benzo[1,4]dioxine-5-yl)-piperazine-1-yl)-ethyl-methyl-amino)-2-methyl-2H-pyridazine-3-one;
4-chloro-5-({2-[4-(2,3-dihydro-benzo[1,4]dioxine-5-yl)-piperazine-1-yl]-ethyl}-methyl-amino)-2-methyl-2H-pyridazine-3-one;
5-{2-[2-(2,3-dihydro-benzo[1,4]dioxine-5-yl-oxy)-ethyl-amino]-ethyl-amino}-2-methyl-2H-pyridazine-3-one.

In case of processes (a), (b), (c), (d) and (e) of the invention, the reactions are carried out in a manner similar to the known analogous processes, see e.g. March, J.: Advanced Organic Chemistry, Reactions, Mechanism and Structure, $4^{th}$ Edition, John Wiley and Sons, New York, 1992.

In process (e) of the invention, usually, a mixture of the compounds of the general Formula I is formed, that is a mixture of the compound, wherein X represents a group of the Formula II and Y stands for halogen, and the one, wherein X represents halogen and Y stands for a group of the general Formula II, depending on the starting substances used. The components of the mixture are separated by conventional methods of the preparative organic chemistry e.g. fractionated crystallization.

When a substituted alkylaminopyridazinone derivative of the Formula I, wherein X or Y stands for halogen, preferably chlorine, is subjected to catalytic hydrogenation, then dehalogenation proceeds and the corresponding substituted alkylaminopyridazinone derivative of the general Formula I or its hydrochloride salt, wherein X or Y stands for hydrogen, is formed.

The catalytic hydrogenation is carried out in an analogous manner as the processes described in the literature [e.g. March, J.: Advanced Organic Chemistry, Reactions, Mechanism and Structure $4^{th}$ Edition, John Wiley and Sons, New York, 1992]. As the hydrogen source, for example, hydrogen gas, hydrazine, hydrazine hydrate, formic acid, a trialkylammonium formate or an alkali metal formate can be used. The catalyst is suitably palladium, platinum oxide, Raney nickel etc. The reaction can be performed in the presence or absence of an acid binding agent. As acid binding agent, an inorganic base such as sodium hydroxide or an organic base such as hydrazine, triethyl amine, diisopropyl ethyl amine etc. can be used. The reaction can be carried out in an indifferent protic or aprotic solvent or a mixture thereof. The protic solvent is, for example, an alkanol, water or mixtures thereof, the aprotic solvent is suitably dioxane, tetrahydrofurane or dichloro methane. In general, the reaction temperature is 0–150° C., preferably 20–100° C.

The preparation of the acid addition salt from the free base of the Formula I and the liberation of the base from the acid addition salt are carried out in a manner known per se.

The alkylaminopyridazinone derivatives of the Formulae III and V used as the starting compounds can be prepared by the process described in the International Patent Application No. PCT/HU98/00054 (WO 99/64402).

The amines of the Formula IV are partly known compounds. The novel ones can be prepared in an analogous way [Pollard et al., J. Am. Chem. Soc., 56, 2199 (1934)].

A part of the aminoalkylaminopyridazinone derivatives of the Formulae VI and VIII is also known from the literature. The novel compounds can be prepared in an analogous manner as described in the literature [Haerer et al., Arzneim. Forsch., 39(6), 714–716 (1989)].

The compounds of the Formula VII are partly known, too. The novel compounds can be prepared by employing the methods described in the literature [Augstein, J. et al., J. Med. Chem., 8, 356–367 (1965)].

The dihalopyridazinone derivatives of the Formula IX are partly known. The novel compounds can be prepared by using the methods known from the literature [Homer et al., J. Chem. Soc., 1948, 2194].

The compounds of the Formula X can be prepared from the corresponding amine of the Formula IV in a manner known per se [Shigenaga, S. et al., Arch. Pharm., 329(1), 3–10 (1996); Janssens, F. et al., J. Med. Chem., 28(12), 1934–1943 (1985); He Xiao Shu et al., Bioorg. Med. Chem. Lett., 7(18), 2399–2402 (1997)].

The pharmacological effect of the substituted alkylaminopyridazinone derivatives of the general Formula I was studied on the following tests.

Anxiolytic Effect

Vogel Lick-conflict

Experiments were performed in a PC operated system (LIIKOSYS, Experimentria, Hungary) consisted of 8 test chambers (20 cm×20 cm×20 cm Plexiglas boxes) each of which was equipped with a water fountain system mounted at appropriate height on the wall of the chamber and metal grid floor for delivering electric shocks. 160–180 g male Wistar rats N=8) were deprived of drinking water 48 h and fasted for 24 h prior to test. Test and reference compounds or vehicle were administered intraperitoneally, 30 min prior to test. All procedures were carried out in a quiet, air-conditioned room between 07:30 and 13:00 h at an ambient temperature of 23±2° C. At the beginning of the test the animals were placed in the test chamber where they had free access to drinking water for a 30 s grace period. After that, electric shocks (600 μA, 0.6 s) were applied through the drinking spout following every 20 licks during the 5 min test period (Vogel et al, 1971). Number of punished licks were recorded and stored by an IBM compatible computer. Means±SEM of numbers of tolerated shocks were calculated in each group, statistical analysis of data was performed by one way ANOVA followed by Duncan's test (STATISTICA). The results obtained are shown in Table 1. Diazepam [7-chloro-1,3-dihydro-1-methyl-5-phenyl-2H-1,4-benzodiazepine-2-one] was used as the reference substance.

TABLE 1

Vogel's drinking conflict test

| Compound (Example No.) | MED in mg/kg ip. |
|---|---|
| 2 | 20.0 |
| 4 | 20.0 |
| 6 | <5.0 |
| 7 | <10.0 |
| 10 | 5.0 |
| 11 | 20.0 |
| Diazepam | 5.0 |

The data of table 1 indicate that the substituted alkylaminopyridazinone derivatives of the Formula I have significant anxiolytic effect equivalent to that of diazepam.

Elevated Plus-maze Test in Rats

Tests have been performed as described by Pellow and co-workers [J. Neurosci. Methods, 14, 149 (1985)]. A wooden cross, 15 cm wide with 100 cm long arms was used for the experiments. The sides and ends of two opposite arms of the cross were equipped with 40 cm high walls, however, the arms were open to the 15×15 cm central area (closed arms). The two other opposite arms were not encircled by walls (open arms).

Male Sprague-Dawley rats weighing 200–220 g were used for the experiments. The animals were placed in the central area of the equipment 60 min after treatment and the following four parameters have been observed for the 5 min test time:

time spent in the open arms, time spent in the closed arms, number of entries into the open arms, number of entries into the closed arms.

The effect was expressed as percent increase in either the time (measured in sec) spent in the open arms or number of entries into the open arms. MEDs (minimal effective dose) were determined for each compound regarding the time spent in the open arms. The results obtained are summarized in Table 2. Buspirone [8-{4-[4-(2-pyrimidinyl)-1-piperazinyl]butyl}-8-azaspiro[4,5]decane-7,9-dione] was used as the reference substance.

TABLE 2

Elevated plus-maze test in rats

| Compound (Example No.) | MED in mg/kg po. |
|---|---|
| 2 | 10.0 |
| 3 | 10.0 |
| 4 | 1.0 |
| 5 | 0.003 |
| 9 | 0.3 |
| 10 | 0.01 |
| Buspirone | 3.0 |

From Table 2 it is evident that the substituted alkylaminopyridazinone derivatives of the Formula I have outstanding anxiolytic activity in the above test, considerably exceeding the efficacy of the reference substance.

Sedative Effect

Inhibition of Spontaneous Motor Activity

The effect on spontaneous motor activity was investigated according to Borsy and co-workers [Borsy, J. et al, Arch. Int. Pharmacodyn., 124, 180–190 (1960)] in a ten channel Dews instrument, with 1-1 animal in each channel. Animals were placed into the instrument 60 min after per os treatment with either vehicle or test compound, and interruptions of infrared beams were recorded for 30 min. From these data, 50 per cent. Inhibitory doses ($ID_{50}$)have been determined by regression analysis. The results obtained are shown in Table 3. Diazepam was used as the reference substance.

TABLE 3

Inhibition of spontaneous motility in mouse

| Compound (Example No.) | $ID_{50}$ in mg/kg po. |
|---|---|
| 4 | 30.0 |
| 5 | 11.0 |
| 9 | >30.0 |
| 10 | 53.3 |
| Diazepam | 7.0 |

In contrast to the diazepam used as the reference substance, the tested substituted alkylaminopyridazinone derivatives of the Formula I display sedative effect only in a relatively high dose.

Effects on Blood Pressure

The experiments were performed in conscious, freely moving, male Wistar rats using a radiotelemetry system (Data Sciences International, St. Paul, Minn., USA). Prior to treatments rats were implanted with transmitters (type: TL11M2-C50-PXT) that permitted continues monitoring of arterial blood pressure. Under sterile surgical conditions, catheter of the transmitter was introduced into the abdominal aorta for measurement of arterial blood pressure and the transmitter was sutured to the abdominal wall of animals anaesthetised with pentobarbital-Na (60 mg/kg, i.p.; Nembutal inj. Phylaxia-Sanofi, Budapest). After surgery the animals were treated with an antibiotic (1 ml/kg i.m. Tardomyocel comp. inj. ad us. vet., Bayer A G, Leverkusen, Germany). A 7 day postoperative recovery period was allowed. Radio signals emitted by the transmitters were detected by RLA1000 type receivers placed under each animal's cage. The data were collected, saved and evaluated using the Dataquest IV. software from Data Sciences. The computer was set to sample the parameters for 10 seconds in every second minute.

The test substances or vehicle (methyl cellulose 0.4% w/v) were administered orally by gavage in a volume of 1 ml/kg at about 10 a.m. The effects of test items were measured for 6 hours. The effect of each compound was compared with that caused by vehicle treatment using two-way analysis of variance for repeated measures with Scheffe's post hoc test.

Data obtained are shown in the Table 4. None of the compounds examined reduced blood pressure of the test animals.

TABLE 4

Effects of different test compounds or vehicle on mean arterial blood pressure for 6 hours after treatment in conscious rats

| | Mean blood pressure | | | | |
|---|---|---|---|---|---|
| | after treatment with placebo (mmHg) | | after treatment with test compound (mmHg) | | Results of statistical |
| Example | Mean | S.E. | Mean | S.E. | evaluation |
| 8 | 91.5 | 2.9 | 95.4 | 2.2 | N.S. |
| 7 | 96.0 | 2.7 | 97.0 | 2.1 | N.S. |
| 6 | 101.5 | 3.8 | 106.3 | 2.7 | N.S. |
| 12 | 91.5 | 2.9 | 89.9 | 2.5 | N.S. |
| 11 | 91.5 | 2.9 | 101.5 | 3.9 | N.S. |
| 16 | 99.1 | 1.9 | 105.2 | 1.6 | N.S. |

S.E. = Standard Error (of the mean);
N.S. = Not significant statistically (when compared to placebo)

According to data presented here the compounds of present invention have no effect on blood pressure, indicating the lack of antihypertensive potential.

Effect of Cognition and Memory

Male Wistar rats weighing 200–220 g were used. The animals were obtained from Charles River Co. They were kept in a room with normal 12–12 h light-dark cycle (light on: 06:00) at relative humidity of 60±10%.

The experiment was performed in a five-channel "step through"-type passive avoidance learning apparatus. The equipment consisted of two adjacent Plexi-glass boxes of 20×20×16 cm. One of them was made of regular transparent Plexi-glass and the other one was made of black, non-transparent Plexi-glass. The boxes were connected with a 7.5×8 cm passage way, equipped with a computer-controlled guillotine-door. The passage of the rats through the door was detected by infrared photocells arranged in two parallel lines in the opening of the passage way. The door was automatically closed when the animals passed through. The dark compartment was equipped with stainless steel grid floor through which electric foot shocks could have been delivered to the animals. A 10 W light bulb was installed above the passage way in the light compartment.

The experiment was performed on two consecutive days, in two sessions which were 24 h apart from each other.

On Day 1 (Acquisition) the animals acquired information about the situation (grid floor shock in the dark compartment), on Day 2 (Retention) they recalled the acquired information to avoid punishment ("if I go into the dark I will be punished, so I stay outside in the light").

Day 1 (Acquisition)

The individually numbered animals were placed into the light compartment of the equipment. After 30 s the guillotine door was opened and the rats could freely pass to the dark (considered as safe) compartment. Step through latency was automatically determined. (Step-trough latency is the time period spanning from door opening to the time when the animal passed into the dark compartment.) The door was closed then, and the timer was automatically stopped. An electric foot shock of 1.2 mA lasting 2.5 s was applied to the animal through the grid floor 3 s after the door has been closed, except for rats in the absolute control group (no shock+vehicle treated). Test animals were removed from the dark compartment immediately after foot shock has been delivered. The function of the absolute control group was to show that shocked animals will remember the unpleasant foot shock as revealed by increased latency time when compared to absolute control. That is the essence of acquisition.

Day 2 (Retention)

After 24 h, the animals were placed again in the light compartment of the test apparatus and step-through latency was measured as described at Acquisition day, except that no foot shock was applied to the animals in any group on the second day. A maximum of 180 s time interval was available for the rats to pass into the dark compartment. The animals were removed from the light compartment if they did not pass to the dark compartment within the 180 s test period.

The investigators surprisingly found that the invention compounds significantly increased step-through latency into the dark compartment of the passive avoidance apparatus after Day 2 administration of the compound (FIG. 1).

It is shown on FIG. 1 that in absolute control group(no shock, untreated), step-trough latency was approximately the same on both experimental days (meaning that there was nothing to recall and avoid on the second day).

In the shocked, vehicle-treated control group the unavoidable 1.2 mA foot shock resulted in a significantly increased step-through latency on Day 2 when compared to absolute control. The experimental animals recalled the annoying experience (foot shock) in the dark, therefore, they pass into the dark compartment with a significantly longer time (increased latency).

In the treated groups this augmented latency has been further increased after the Day 2 treatment indicating that the retention of memory has been improved.

These surprising effects are not evident since anxiolytic compounds (i.e. diazepam) have a deleterious effect on memory.

From therapeutic point of view the advantageous effect of compounds of general Formula I on learning and memory signifies that the compounds could be appropriate for treating and/or preventing diseases or conditions accompanying diseases wherein learning or memory functions are suffering a loss or there is a possibility to suffering a loss. Such diseases are, but not limited to—as mentioned earlier—Alzheimer's disease, Korsakoff syndrome, Huntington's disease, Parkinson's disease and mental decline due to ageing processes, impairment of the cognitive functions or to exposure to toxic substances as well.

Based on the above test data, the substituted alkylaminopyridazinone derivatives of the general Formula I are effective in the treatment of various clinical patterns connected with anxiety. In case of certain compounds, the anxiolytic potential exceeds by several orders of magnitude the effect of the marketed reference substances (diazepam, buspirone). Sedative side-effect appears only in a dose that is multiple of the one needed to produce the expected therapeutical effect. This means that the substituted alkylaminopyridazinone derivatives of the general Formula I do not have sedative, life quality deteriorating side-effects which are characteristic of benzodiazepines.

Summarized, the compounds of general Formula I surprisingly in an unforeseen manner possess considerable anxiolytic properties without sedative side effects in their anxiolytic dose range. In addition to the the anxiolytic efficacy, the compounds of general Formula I have advantageous effects on cognition and memory. According to our studies the compounds of general Formula I surprisingly have no antihypertensive potential.

Based on the above tests, the compounds of the invention and pharmaceutically suitable acid addition salts thereof can be used as active ingredients in pharmaceutical compositions.

Furthermore, the invention refers to a pharmaceutical composition comprising a substituted alkylaminopyridazinone derivative of general Formula I or a pharmaceutically suitable acid addition salt thereof and one or more conventional carriers.

The pharmaceutical composition of the invention contains, in general, 0.1 to 95 per cent by weight, preferably 1 to 50 per cent by weight, suitably 5 to 30 per cent by weight of the active ingredient.

The pharmaceutical composition of the invention is suitable for peroral, parenteral, rectal or transdermal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinyl-pyrrolidone) etc.; filling agents such as lactose, glucose, starch, calcium phosphate etc.; auxiliary substances for tabletting such as magnesium stearate, talc, poly(ethylene glycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propylene glycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18$^{th}$ Edition, Mack Publishing Co., Easton, USA (1990).

The pharmaceutical composition contains dosage unit, in general. A typical dose for adult patients amounts to 0.1 to 1000 mg of the compound of the Formula I or a pharmaceutically suitable acid addition salt thereof calculated for 1 kg body weight, daily. The daily dose can be administered in one or more portions. The actual dosage depends on many factors and is determined by the physician.

The pharmaceutical composition is prepared by admixing a compound of the Formula I or a pharmaceutically suitable acid addition salt thereof to one or more carrier(s), and converting the mixture obtained to a pharmaceutical composition in a manner known per se. Useful methods are known from the literature, e.g. Remington's Pharmaceutical Sciences mentioned above.

The pharmaceutical composition containing a substituted alkylaminopyridazinone derivative of the Formula I or a pharmaceutically suitable acid addition salt thereof is prepared in a similar way as the pharmaceutical composition containing the novel substituted alkylaminopyridazinone derivative of the Formula I or a pharmaceutically suitable acid addition salt thereof as the active ingredient.

Further details of the present invention are to be found in the following Examples without limiting the scope of protection to said Examples.

EXAMPLES

Example 1

Preparation of 5-chloro-4-(3-((2-(2,3-dihydrobenzo [1,4]dioxine-5-yloxy)-ethyl)methyl-amino)-propyl-amino)-2H-pyridazine-3-one oxalate A mixture of 2.66 g (0.01 moles) of 4-(3-bromopropylamino)-5-chloro-2H-pyridazine-3-one, 2.51 g (0.012 moles) of 2-(2,3-dihydrobenzo[1,4]dioxine-5-yloxy) ethylmethylamine, 2.8 cm$^3$ (0.02 moles) of triethylamine and 40 cm$^3$ of acetone is stirred at reflux temperature under reflux for 120 hours. Then, the reaction mixture is cooled, filtered, and the mother liquor is evaporated under reduced pressure. The residue obtained is subjected to chromatography over a silica gel column using a 1:1:2 mixture of acetone, ethyl acetate and chloroform as the eluent. The fractions containing the active substance are collected, evaporated, and the residue is dissolved in a 15:1 mixture of diethyl ether and ethyl acetate. To the solution obtained, a solution of oxalic acid in diethyl ether is added, drop by drop, at room temperature under stirring. The crystals obtained are filtered and washed with diethyl ether.

Thus, 2.76 g (57.0%) of the title compound are obtained. M.p.: 115–117° C.

Analysis: for $C_{20}H_{25}ClN_4O_8$ (484.90); calc.: C, 49.54%; H, 5.20%; Cl, 7.31%; N, 11.55%; found: C, 49.04%; H, 5.11%; Cl, 7.18%; N, 11.42%.

IR (KBr): 3300, 1720, 1640, 1610, 1114.

$^1$H-NMR (DMSO-d$_6$, i400): 12.8 (b, 1H), 7.60 (s, 1H), 6.77 (bt, J=6.7 Hz, 1H), 6.74 (~t, J=8.2 Hz, 1H), 6.60 (dd, J1=1.5 Hz, J2=8.3 Hz, 1H), 6.53 (dd, J1=1.4 Hz, J2=8.2 Hz, 1H), 4.27 (t, J=5.1 Hz, 2H), 4.22 (s, 4H), 3.69 (~q, J=6.7 Hz, 2H), 3.38 (t, J=5.0 Hz, 2H), 3.10 (~t, J=7.7 Hz, 2H), 2.78 (s, 3H), 1.95 (m, 2H).

Example 2

Preparation of 5-chloro-4-(3-{[2-(2,3-dihydrobenzo [1,4]dioxine-5-yloxy)-ethyl]propyl-amino}propylamino)-2H-pyridazine-3-one A mixture of 1.33 g (0.005 moles) of 4-(3-bromopropylamino)-5-chloro-2H-pyridazine-3-one, 1.42 g (0.006 moles) of (2-(2,3-dihydrobenzo[1,4]dioxine-5-yloxy)ethyl)propylamine, 1.01 g (0.01 moles) of triethylamine and 20 cm³ of acetone is stirred under reflux at reflux temperature for 32 hours. Then, the reaction mixture is cooled, filtered, and the mother liquor is evaporated under reduced pressure. The residue obtained is subjected to chromatography over a silica gel column using a 1:1 mixture of acetone and ethyl acetate. The fractions containing the active substance are collected, evaporated, and suspended in diisopropyl ether. The crystals obtained are filtered, and washed with diethyl ether.

Thus, 1.52 g (72.0%) of the title compound are obtained. M.p.: 87–89° C.

Analysis: for $C_{20}H_{27}ClN_4O_4$ (422.92); calc.: C, 56.80%; H, 6.44%; Cl, 8.38%; N, 13.25%; found: C, 56.48%; H, 6.62%; Cl, 8.17%; N, 13.01%;

IR (KBr): 3328, 1642, 1612.

$^1$H-NMR (CDCl$_3$, g200): 11.05 (b, 1H), 7.49 (s, 1H), 6.71 (m, 1H), 6.49 (m, 2H), 6.60 (bt, J=6.6 Hz, 1H), 4.27 (m, 4H), 4.12 (t, J=6.4 Hz, 2H), 3.87 (~q, J=6.4 Hz, 2H), 2.93 (t, J=6.4 Hz, 2H), 2.69 (t, J=6.2 Hz, 2H), 2.51 (~t, J=7.6 Hz, 2H), 1.80 (~qn, J=6.4 Hz, 2H), 1.54 (~bx, J=7.5 Hz, 2H), 0.89 ((t, J=7.3 Hz, 3H).

$^{13}$C-NMR (CDCl$_3$, g200): 157.77, 148.22, 144.26, 140.86, 140.19, 133.51, 120.05, 110.00, 106.77, 105.41, 67.50, 64.38, 64.17, 57.13, 53.01, 52.87, 43.40, 28.12, 20.19, 11.80.

Example 3

Preparation of 4-{3-[benzyl-[2-(2,3-dihydrobenzo[1,4]dioxine-5-yloxy)ethyl]-amino]propylamino}-5-chloro-2H-pyridazine-3-one hydrochloride A mixture of 5.3 g (0.02 moles) of 4-(3-bromopropylamino)-5-chloro-2H-pyridazine-3-one, 7.82 g (0.027 moles) of benzyl-[2-(2,3-dihydro-benzo[1,4]dioxine-5-yloxy)ethyl]amine, 5.6 cm³ (0.04 moles) of triethylamine and 150 cm³ of acetone, is stirred at reflux temperature under reflux for 24 hours. Then, the reaction mixture is evaporated under reduced pressure. The residue obtained is dissolved in 200 cm³ of ethyl acetate, extracted once with 100 cm³ of water, once with 30 cm³ of 10% aqueous sodium hydroxide solution, and twice with 50 cm³ of water. The organic phase is dried over anhydrous magnesium sulfate, filtered, and evaporated under reduced pressure. The residue is subjected to chromatography over a silica gel column using a 4:3:5:0.2 mixture of ethyl acetate, hexane, chloroform and methanol. The fractions containing the active substance are collected, evaporated, and the residue is dissolved in a 30:1 mixture of diethyl ether and ethyl acetate. To the solution, diethyl ether containing hydrogen chloride are added, drop by drop, under stirring at room temperature. The crystals obtained are filtered and washed with diethyl ether.

Thus, 3.65 g (36.0%) of the title compound are obtained. M.p.: 207–209° C.

Analysis: for $C_{24}H_{28}Cl_2N_4O_4$ (507.42); calc.: C, 56.81%; H, 5.56%; Cl, 13.97%; N, 11.04%; found: C, 56.24%; H, 5.51%; Cl, 13.90%, N 10.74%.

IR (KBr): 2931, 1641, 1607.

$^1$H-NMR (DMSO-d$_6$, i400): 12.79 (s, 1H), 11.22 (bs, 1H), 7.66 (m, 2H), 7.59 (m, 3H), 7.40 (m, 3H), 6.76 (~t, 1H), 6.72 (~t, 1H), 6.60 (dd, 1H), 6.54 (dd, 1H), 4.46 (m, 5H), 4.22 (s, 4H), 3.68 (m, 2H), 3.48 (m, 2H), 3.18 (m, 2H), 2.10 (m, 2H).

$^{13}$C-NMR(CDCl$_3$, i400): 156.87, 147.11, 144.35, 139.72, 139.44, 133.81, 131.47, 130.07, 129.53, 128.83, 120.13, 110.79, 106.54, 106.37, 64.09, 64.06, 63.79, 56.74, 50.67, 49.58, 40.25, 24.98.

Example 4

Preparation of 5-chloro-4-{4-[4-(2,3-dihydrobenzo[1,4]dioxine-5-yl)-piperazine-1-yl]-butylamino}-2H-piridazine-3-one A mixture of 1.65 g (0.01 moles) of 4,5-dichloro-2H-pyridazine-3-one, 7.28 g (0.025 moles) of 4-(4-(2,3-dihydrobenzo[1,4]-dioxine-5-yl)-piperazine-1-yl)-butylamine and 40 cm³ of dioxane is stirred at reflux temperature under reflux for 24 hours. Then, the reaction mixture is evaporated under reduced pressure. The residue obtained is dissolved in toluene, extracted with a 10% aqueous sodium carbonate solution, then several times with water. The organic phase is dried over anhydrous magnesium sulfate, filtered, and the filtrate is evaporated under reduced pressure. The residue obtained is subjected to chromatography over a silica gel column using a 3:2:0.5 mixture of hexane, acetone and methanol as the eluent. The fractions containing the active substance are collected and evaporated. The residue is rubbed with diethyl ether, the formed crystals are filtered.

Thus, 1.91 g (45,6%) of the title compound are obtained. M.p.: 160–162° C.

Analysis: for $C_{20}H_{25}ClN_5O_3$ (419.92); calc.: C, 57.21%; H, 6.24%; Cl, 8.44%; N, 16.68%; found: C, 57.26%; H, 6.32%; Cl, 8.33%; N, 16.49%.

IR(KBr): 3345, 1648, 1613.

$^1$H-NMR (CDCl$_3$, i400): 11.02 (bs, 1H), 7.52 (s, 1H), 6.77 (t, 1H, J=8.1 Hz), 6.59 (dd, 1H, J1=1.4 Hz, J2=8.2 Hz), 6.54 (dd, 1H, J1=1.5 Hz, J2=8.0 Hz), 5.89 (m, 1H), 4.28 (m, 4H), 3.77 (~q, 2H, J=6.7 Hz), 3.11 (m, 4H), 2.67 (m, 4H), 2.46 (t, 2H, J=7.0 Hz), 1.68 (m, 4H).

Example 5

Preparation of 4-chloro-5-{2-[4-(2,3-dihydrobenzo[1,4]dioxine-5-yl)-piperazin-1-yl]-ethylamino}-2H-pyridazine-3-one A mixture of 1.33 g (0.006 moles) of 1-(2,3-dihydro-1,4-benzodioxine-5-yl)-piperazine, 4.5 cm³ of dimethylformamide, 2 cm³ (0.014 moles) of triethylamine, 0.1 g (0.0006 moles) of potassium iodide és 1.23 g (0,0049 moles) of 5-(2-bromo-ethylamino)-4-chloro-2H-pyridazine-3-one is stirred for 4 hours at room temperature. Then, a solution prepared from 33 cm of water and 1.2 g (0.014 moles) of sodium hydrogen carbonate is added. Due to the water, a precipitate is formed. The crystals are filtered, and washed several times with water. The crude product is dissolved in acetonitrile under stirring at reflux temperature, filtered, and the filtrate is evaporated to the fifth of the original volume. Then, the solution is stirred under cooling with ice water, and the crystals obtained are filtered.

Thus, 1.51 g (78.6%) of the title compound are obtained. M.p.: 217–219° C.

Analysis: for $C_{18}H_{22}ClN_5O_3$ (391.86); calc.: C, 55.17%; H, 5.66%; Cl, 9.05%; N, 17.87%; found: C, 54.99%;H 5.68%; Cl, 8.80%,N 18.16%.

IR (KBr): 3360, 1637, 1602.

$^1$H-NM (CDCl$_3$, i400): 11.38 (bs, 1H), 7.63 (s, 1H), 6.78 (t, 1H, J=8.1 Hz), 6.61 (dd, 1H, J1=1.5 Hz, J2=8.2 Hz), 6.55 (dd, 1H, J1=1.5 Hz, J2=8.0 Hz), 5.80 (bs, 1H), 4.29 (m, 4H), 3.43 (m, 2H), 3.12 (m, 4H), 2.74 (m, 6H).

Example 6

Preparation of 4-chloro-5-{2-[4-(2,3-dihydro-1,4-benzodioxine-5-yl)-piperazine-1-yl]-ethylamino}-2-methyl-2H-piridazine-3-one monohydrate A mixture of 1.31 g (0.0059 moles) of 4-chloro-5-(2-chloroethylamino)-2-methyl-2H-pyridazine-3-one, 1.5 g (0.0068 moles) of 1-(2,3-dihydro-benzo[1,4]dioxine-5-yl)piperazine, 1.68 g (0.012 moles) of potassium carbonate, 0.2 g of potassium iodide and 34 cm$^3$ of acetonitrile is stirred at reflux temperature under reflux for 48 hours. The reaction mixture is filtered, the filtrate is evaporated under reduced pressure, the residue obtained is, at first, recrystallized from 2-propanol, then from acetonitrile.

Thus, 1.25 g (71.1%) of the title compound are obtained. M.p.: 132–134° C.

Analysis: for $C_{19}H_{26}ClN_5O_3$ (492.83); calc.: C, 53.84%; H, 6.18%; Cl, 8.36%; N, 16.52%; found: C, 54.02%; H, 6.39%; Cl, 8.37%; N, 16.71%.

IR (KBr): 3335, 1633, 1263.

$^1$H-NMR (DMSO-d$_6$, i400): 7.87 (s, 1H), 6.70 (~t, J=8.1 Hz, 1H), 6.49 (dd, J1=1.1 Hz, J2=8.2 Hz, 1H), 6.44 (dd, J1=1.1 Hz, J2=8.0 Hz, 1H), 6.36 (bt, J=5.8 Hz, 1H), 4.22 (m, 2H), 4.19 (m, 2H), 3.58 (s, 3H), 3.45 (~q, J=6.1 Hz, 1H), 2.94 (m, 4H), 2.57 (m, 6H).

$^{13}$C-NMR (DMSO-d$_6$, i400): 156.89, 144.75, 143.99, 141.71, 136.33, 126.82, 120.47, 111.20, 110.35, 104.68, 63.97, 63.87, 57.17, 53.03, 50.34, 39.62.

Example 7

Preparation of 4-chloro-5-{2-[4-(2,3-dihydrobenzo[1,4]dioxine-5-yl)-piperazine-1-yl]ethyl}methylamino-2H-pyridazine-3-one A mixture of 4.65 g (0.021 moles) of 4-chloro-5-[(2-chloroethyl)-methylamino]-2H-piridazine-3-one, 6.6 g (0.03 moles) of 1-(2,3-dihydrobenzo[1,4]dioxine-5-yl)piperazine, 5.1 cm$^3$ of triethyl-amine and 12 cm$^3$ of dimethylformamide is stirred at reflux temperature under reflux for 48 hours. Then, water is added to the reaction mixture, the pH is adjusted to 10 by the addition of aqueous sodium hydroxide solution, and the aqueous phase is extracted twice with dichloromethane. The combined organic phases are washed with water several times, dried over anhydrous magnesium sulfate, filtered, and the filtrate is evaporated under reduced pressure. The residue is subjected to chromatography over a silica gel column using a 2:1:0.5 mixture of ethyl acetate, hexane and methanol as the eluent. The fractions containing the active substance are collected, evaporated, the residue is suspended in diethyl ether. The crystals obtained are filtered.

Thus, 2.4 g (28.2%) of the title compound are obtained. M.p.: 214–215° C.

Analysis: for $C_{19}H_{24}ClN_5O_3$ (405.89); calc.: H, 5.96%; Cl, 8.73%; N, 17.25%; found: H, 5.68%; Cl, 8.94%; N, 16.89%.

IR (KBr): 2827, 1641, 1596.

$^1$H-NMR (DMSO-d$_6$, g200): 12.71 (bs, 1H), 7.86 (s, 1H), 6.70 (~t, J=8.1 Hz, 1H), 6.48 (dd, J1=1.5 Hz, J2=8.3 Hz, 1H), 6.38 (dd, J1=1.5 Hz, J2=8.3 Hz, 1H), 4.20 (~s, 4H), 3.59 (t, J=6.1 hz, 2H), 3.06 (s, 3H), 2.81 (m, 4H), 2.56 (t, J=6.3 Hz, 2H), 2.48 (m, 4H).

$^{13}$C-NMR (DMSO-d$_6$, g200):158.91, 148.77, 144.00, 141.68, 136.31, 132.43, 120.47, 111.21, 110.90, 110.26, 63.97, 55.09, 53.06, 50.29, 40.95, 40.53.

Example 8

Preparation of 2-tert.-butyl-5-chloro-4-{2-[4-(2,3-dihydrobenzo-[1,4]dioxine-5-yl)piperazine-1-yl] ethylamino}-2H-pyridazine-3-one A mixture of 2.71 g (0.00122 moles) of 2-tert-butyl-4,5-dichloro-2H-pyridazine-3-one, 4.67 g (0.0177 moles) of 2-[4-(2,3-dihydrobenzo[1,4]-dioxine-5-yl)piperazine-1-yl] ethylamin, 60 cm$^3$ of dioxane and 3.3 g of potassium carbonate is stirred at reflux temperature under reflux for 24 hours. Then, the reaction mixture is filtered, the filtrate is evaporated under reduced pressure, the residue is subjected to chromatography over a silica gel column using a 2:1 mixture of hexane and acetone as the eluent. The fractions containing the active substance are collected, evaporated, the residue is suspended in diisopropyl ether, and the crystals obtained are filtered.

Thus, 1.34 g (24.5%) of the title compound are obtained. M.p.: 177–178° C.

Analysis: for $C_{22}H_{30}ClN_5O_3$ (447.97); calc.: C, 58.99%; H, 6.75%; Cl, 7.91%; N, 15.63%; found: C, 58.78%; H, 6.66%; Cl, 7.80%; N, 15.35%.

IR (KBr): 3321, 1602, 1475, 1143, 998.

$^1$H-NMR (CDCl$_3$, i400): 7.45 (s, 1H), 6.77 (~t, J=8.1 Hz, 1H), 6.59 (d, J=8 Hz, 1H), 6.54 (d, J=8.0 Hz, 1H), 6.35 (bt, 1H), 4.31 (m, 2H), 4.24 (nm, 2H), 3.87 (~q, J=5.6 Hz, 2H), 3.13 (m, 4H), 2.71 (m, 6H), 1.62 (s, 9H).

$^{13}$C-NMR(CDCl$_3$, i400): 156.44, 144.02, 141.58, 140.32, 137.37, 136.38, 120.60, 111.90, 110.74, 106.2, 64.73, 64.29, 63.91, 57.57, 53.01, 50.48, 40.53, 27.84.

Example 9

Preparation of 4-{3-[2-(2,3-dihydrobenzo[1,4]dioxine-5-yloxy)ethylamino]-propylamino}-2H-pyridazine-3-one 12.52 g (0.027 moles) of 4-(3-{benzyl-[2-(2,3-dihydrobenzo-[1,4]dioxine-5-yloxy)ethylamino]propylamino}-5-chloro-2H-pyridazine-3-one, 420 cm$^3$ of methanol, 1.2 g (0.03 moles) of sodium hydroxide and 12.5 g of palladium on carbon catalyst consisting of 8% of Pd, 28% of C and 64% of H$_2$O are transferred into an autoclave. The reaction mixture is stirred at room temperature and under a hydrogen pressure of 10 atm for 48 hours. Then, the excess hydrogen is let out from the autoclave, the reaction mixture is filtered, and the catalyst is washed three times using 100 cm$^3$ of water each time. The filtrate is evaporated under reduced pressure, and the residue is subjected to chromatography over a silica gel column using a 4:1 mixture of dichloromethane and methanol as the eluent. The fractions containing the active substance are combined, evaporated, the residue is suspended in diisopropyl ether. The crystals obtained are filtered.

Thus, 5.92 g (63.4%) of the title compound are obtained. M.p.: 118–120° C.

IR (KBr): 3289, 1646, 16136, 1112.

$^1$H-NMR (DMSO-d$_6$, i400): 12.50 (b, 1H), 7.55 (d, J=4.9 Hz, 1H), 6.79 (bt, J=5.9 Hz, 1H), 6.74 (~t, J=8.2 Hz, 1H), 6.60 (dd, J1=1.4 Hz, J2=8.2 Hz, 1H), 6.53 (dd, J1=1.5 Hz, J2=8.2 Hz, 1H), 6.09 (d, J=4.9 Hz, 1H), 4.22 (s, 4H), 4.18 (t, J=5.4 Hz, 2H), 3.21 (~q, J=6.3 Hz, 2H), 3.16 (t, J=5.4 Hz, 2H), 2.92 (t, J=7.3 Hz, 2H), 1.87 (~qn, J=7.1 Hz, 2H).

Hydrochloride of the title compound

M.p.: 203–204° C.

Analysis: for $C_{17}H_{23}ClN_4O_4$ (382.85); calc.: C, 53.23%; H, 6.06%; Cl, 9.26%; N, 14.63%; found: C, 53.26%; H, 6.05%; Cl, 9.14%; N, 19.41%.

¹H-NMR (DMSO-d₆, i400): 12.50 (b, 1H), 7.55 (d, J=4.9 Hz, 1H), 6.79 (bt, J=5.9 Hz, 1H), 6.74 (~t, J=8.2 Hz, 1H), 6.60 (dd, J1=1.4 Hz, J2=8.2 Hz, 1H), 6.53 (dd, J1=1.5 Hz, J2=8.2 Hz, 1H), 6.09 (d, J=4.9 Hz, 1H), 4.22 (s, 4H), 4.18 (t, J=5.4 Hz, 2H), 3.21 (~q, J=6.3 Hz, 2H), 3.16 (t, J=5.4 Hz, 2H), 2.92 (t, J=7.3 Hz, 2H), 1.87 (~qn, J=7.1 Hz, 2H).

Example 10

Preparation of 5-{2-[4-(2,3-dihydro-1,4-benzodioxine-5-yl)-piperazine-1-yl]-ethylamino}-2H-pyridazine-3-one 3.9 g (0.01 moles) of 4-chloro-5-{2-[4-(2,3-dihydro-1,4-benzodioxine-5-yl)piperazine-1-yl]ethylamino}-2H-pyridazine-3-one, 400 cm³ of a 9:1 mixture of methanol and distilled water, 0.45 g (0.0112 moles) of sodium hydroxide and 4 g of palladium catalyst consisting of 8% of Pd, 28% of C and 64% of H₂O are weighed into an autoclave. The reaction mixture is stirred at room temperature and under a hydrogen pressure of 10 atm for 3 hours. Then, the excess hydrogen is let out from the autoclave, the reaction mixture is heated to reflux temperature and stirred at this temperature for 5 minutes, then filtered while hot, and the catalyst is washed three times using 33 cm³ of a 1:1 mixture of methanol and dichloromethane each time. The combined filtrates are evaporated to a volume of 30 cm³, the solution obtained is stirred for half an hour under cooling with ice water, the crystals obtained are filtered and washed with 10 cm³ of cooled methanol. The product is dried at 140° C. over phosphorus pentoxide in vacuo for 3 hours.

Thus, 2.92 g (81.7%) of the title compound are obtained. M.p.: 244–246° C.

Analysis: for $C_{18}H_{23}N_5O_3$ (357.42); calc.: C, 60.49%; H, 6.49%; N, 19.59%; found: C, 60.33%; H, 6.44%; N, 19.46%.

IR (KBr): 3325, 3277, 1612.

¹H-NMR (CDCl₃, i400): 11.85 (bs, 1H), 7.44 (d, J=2.1 Hz, 1H), 6.80 (bt, 1H), 6.66 (~t, J=8.1 Hz, 1H), 6.44 (d, J=8.2 Hz, 1H), 6.41 (d, J=8.1 Hz, 1H), 5.35 (~s, 1H), 4.16 (m, 2H), 3.08 (~q, J=5.4 Hz, 2H), 2.92 (m, 4H), 2.51 (m, 6H).

¹³C-NMR(CDCl₃, i400): 162.31, 149.38, 143.99, 141.75, 136.34, 131.65, 120.48, 111.19, 110.33, 94.32, 63.98, 63.88, 55.91, 53.13, 50.16, 39.15.

Hydrochloride of the title compound

IR (KBr): 3250, 2591, 1085.

¹H-NMR (DMSO-d₆, i400): 12.04 (bs, 1H), 11.33 (bs, 1H), 7.49 (m, 1H), 6.76 (t, J=8.1 Hz, 1H), 6.58 (dd, J1=1.2 Hz, J2=8.2 Hz, 1H), 6.52 (dd, J1=1.1 Hz, J2=7.9 Hz, 1H), 5.62 (d, J=2.3 Hz, 1H), 4.25 (m, 2H), 4.23 (m, 2H), 3.7–3.0 (m, 12H).

¹³C-NMR (DMSO-d₆, i400): 162.31, 148.86, 144.15, 140.02, 136.30, 131.55, 120.65, 112.14, 110.59, 95.44, 64.12, 63.92, 53.29, 51.42, 47.06, 36.19.

Example 11

Preparation of 5-{2-[4-(7-chloro-2,3-dihydrobenzo[1,4]dioxine-5-yl)-piperazine-1-yl]ethylamino}-2H-pyridazine-3-one A mixture of 3.24 g (0.0127 moles) of 1-(7-chloro-2,3-dihydro-benzo-[1,4]dioxine-5-yl)piperazine, 5 cm³ of dimethylformamide, 3.6 cm³ of triethylamine and 1.82 g (0.0086 moles) of 5-(2-chloroethylamino)-2H-pyridazine-3-one hydrochloride is stirred at reflux temperature for 2 hours. To the reaction mixture, a solution of 3.17 g of sodium hydrogen carbonate in 50 cm³ of water is added, drop by drop. Due to the presence of the water, oil separates. The water is decanted from the oil, and 30 cm³ of dichloromethane are added to the residue. The crystals separating under stirring are filtered.

Thus, 1.35 g (27.2%) of the title compound are obtained. M.p.: 115–117° C.

Analysis: for $C_{18}H_{22}ClN_5O_3$ (391.86); calc.: H, 5.66%; Cl, 9.05%; N, 17.87%; found: H, 5.68%; Cl, 9.14%; N, 17.23%.

IR (KBr): 3266, 1616, 1066, 1005.

¹H-NMR (DMSO-d₆, i400): 11.89 (bs, 1H), 7.50 (d, J=2.4 Hz, 1H), 6.90 (b, 1H), 6.58 (d, J=2.4 Hz, 1H), 6.45 (d, J=2.4 Hz, 1H), 5.40 (d, J=1.70 Hz, 1H), 4.24 (~s, 4H), 3.14 (q, J=5.1 Hz, 2H), 3.00 (m, 4H), 2.57 (m, 6H).

¹³C-NMR (DMSO-d₆, i400): 162.32, 149.38, 144.45, 142.61, 135.14, 131.66, 124.32, 110.69, 110.44, 94.33, 64.12, 63.96, 55.80, 52.92, 49.82, 39.08.

Example 12

Preparation of 5-{3-[4-(2,3-dihydro-1,4-benzodioxine-5-yl)piperazine-1-yl]-propylamino}-2H-pyridazine-3-one 2.94 g (0.007 moles) of 4-chloro-5-{3-[4-(2,3-dihydro-1,4-benzodioxine-5-yl)-piperazine-1-yl]propylamino}-2H-pyridazine-3-one, 300 cm³ of a 9:1 mixture of methanol and water and 3 g of palladium on carbon catalyst consisting of 8% of Pd, 28% of C and 64% of H₂O are weighed into an apparatus of 1000 cm³ volume equipped with a reflux condenser connected to a bubbling device. 1.5 cm³ of hydrazine hydrate are added, drop by drop, to the reaction mixture that is then stirred at reflux temperature for 2 hours. The mixture is filtered, and the catalyst is washed three times using 33 cm³ of a 1:1 mixture of methanol and dichloromethane. The combined filtrates are evaporated, and the residue is dissolved in 90 cm³ of a 1:1 mixture of 2-propanol and water under heating, the solution is filtered, and the filtrate is evaporated to the half of the original volume. After cooling, the crystals separated are stirred for flirter half an hour under cooling with ice water, then filtered and washed with diethyl ether. The product is dried at 60° C. over phosphorus pentoxide in vacuo for 3 hours.

Thus, 2.16 g (83.1%) of the title compound are obtained. M.p.: 158–160° C.

Analysis: for $C_{19}H_{25}N_5O_3$ (371.44); calc.: C, 61.44%; H, 6.78%; N, 18.85%; found: C, 60.98%; H, 6.75%; N, 18.61%.

IR (KBr): 3315, 1614, 1275, 1105.

¹H-NMR (DMSO-d₆, i400): 11.89 (bs, 1H), 7.42 (d, J=2.4 Hz, 1H), 6.99 (bt, J=5.2 Hz, 1H), 6.71 (~t, J=8.1 Hz, 1H), 6.49 (dd, J1=1.3 Hz, J2=8.2 Hz, 1H), 6.46 (dd, J1=1.3 Hz, J2=8.1 Hz, 1H), 5.37 (d, J=2.2 Hz, 1H), 4.23 (m, 2H), 4.20 (m, 2H), 3.03 (~q, J=5.7 Hz, 2H), 2.97 (m, 4H), 2.51 (m, 4H), 2.40 (t, J=6.8 Hz, 2H), 1.70 (qn, J=6.8 Hz, 2H).

¹³C-NMR (CDCl₃, i400): 162.32, 149.46, 143.99, 141.77, 136.33, 131.57, 120.47, 111.17, 110.34, 94.07, 63.98, 63.88, 55.43, 53.14, 50.25, 39.07.

Example 13

Preparation of 5-{2-[2-(2,3-dihydrobenzo[1,4]dioxine-5-yloxy)ethylamino)-ethylamino)-2H-pyridazine-3-one 3.4 g (0.0075 moles) of 5-{2-[benzyl-[2-(2,3-dihydrobenzo-[1,4]dioxine-5-yloxy)ethyl]amino]

ethylamino}-4-chloro-2H-pyridazine-3-one, 170 cm³ of a mixture of ethanol and 70 cm³ of water, and 3.4 g of palladium on carbon catalyst consisting of 8% of Pd, 28% of C and 64% of $H_2O$ are weighed into an apparatus of 500 cm³ volume equipped with a reflux condenser connected to a bubbling device. 6.8 cm³ of hydrazine hydrate are added, drop by drop, to the reaction mixture that is then stirred at room temperature for 1 hour, and at reflux temperature. for 2 hours. The mixture is filtered, and the catalyst is washed three times using 33 cm³ of a 1:1 mixture of methanol and dichloromethane. The combined filtrates are evaporated to a volume of 20 cm², the residue is cooled, the crystals formed are stirred under cooling with water for further half an hour, then filtered and washed with diethyl ether. The crude product obtained is recryystalized from acetonitie.

Thus, 2.26 g (83.1%) of the title compound are obtained. M.p.: 81–83° C.

Analysis: for: $C_{16}H_{20}N_4O_4$ (332.36); calc.: C, 57.82%; H, 6.07%; N, 16.86%; found: C, 57.70%; H, 6.08%; N, 16.78%.

IR (KBr): 3248, 3060, 1616, 1110.

¹H-NMR (DMSO-$d_6$, i400): 11.91 (bs, 1H), 7.46 (d, J=2.5 Hz, 1H), 6.93 (bt, J=5.3 Hz, 1H), 6.71 (~t, J=8.2 Hz, 1H), 6.55 (dd, J1=1.4 Hz, J2=8.2 Hz, 1H), 6.47 (dd, J1=1.4 Hz, J2=8.2 Hz, 1H), 5.41 (d, J=2.6 Hz, 1H), 4.21 (s, 4H), 3.99 (t, J=5.7 Hz, 2H), 3.09 (~q, J=5.9 Hz, 2H), 2.89 (t, J=5.6 Hz, 2H), 2.77 (t, J=6.2 Hz, 2H), 1.97 (b, 1H).

¹³C-NMR (DMSO-$d_6$, i400): 162.39, 149.54, 148.25, 144.23, 133.72, 131.69, 120.06, 109.97, 106.21, 94.20, 68.82, 64.04, 63.92, 48.21, 47.36, 41.95.

Example 14

Preparation of 5-{2-[4-(2,3-dihydro1,4-benzodioxine-5-yl)-piperazine-1-yl]-ethylamino}-2-methyl-2H-pyridazine-3-one A mixture of 3.19 g (0.0145 moles) of 1-(2,3-dihydrobenzo-[1,4]dioxin-5-yl)-piperazine, 80 cm³ of acetonitrile, 5.32 g (0.038 moles) of potassium carbonate, 0.3 g potassium iodide and 2.88 g (0.0129 moles) of 5-(2-chloro-ethylamino)-2-methyl-2H-pyridazine-3-one hydrochloride is stirred at reflux temperature for 48 hours. Then the reaction mixture is cooled to room temperature, and filtered. The filtered matter is dissolved in 100 cm³ of water and 100 cm³ of dichloromethane, the organic phase is separated, the aqueous phase is extracted three times using 50 cm³ of dichloromethane each time. The combined organic phases are washed with 25 cm³ of water saturated with sodium chloride, dried over anhydrous magnesium sulfate, and evaporated under reduced pressure. The residue is recrystallized from acetonitrile.

Thus, 2.8 g (58.6%) of the title compound are obtained. M.p.: 188–190° C.

Analysis: for $C_{19}H_{25}N_5O_3$ (371.44); calc.: C, 61.44%; H, 6.78%; N, 18.85%; found: C, 61.49%; H, 6.76%; N, 18.76%.

IR (KBr): 3281, 1614, 1277.

¹H-N (DMSO-$d_6$, i400): 7.52 (d, J=2.7 Hz, 1H), 6.80 (bt, 1H, 6.71 (~t, J=8.1 Hz, 1H), 6.47 (m, 2H), 5.49 (d, J=2.7 Hz, 1H), 4.22 (m, 2H), 4.20 (m, 2H), 3.46 (s, 3H), 3.13 (~q, J=5.6 Hz, 2H), 2.97 (m, 4H), 2.55 (m, 6H).

¹³C-NMR (DMSO-$d_6$, i400): 161.03, 149.14, 143.99, 141.76, 136.33, 130.98, 120.47, 111.18, 110.32, 94.37, 63.97, 63.87, 55.94, 53.13, 50.18, 39.28, 38.30.

Example 15

Preparation of 5-({2-[4-(2,3-dihydro-benzo[1,4]dioxine-5-yl)-piperazine-1-yl]-ethyl}-methyl-amino)-2H-pyridazine-3-one-hydrochloride-monohydrate Into a pressure-proof hydrogenating apparatus 0.8 g (0.002 mole) of 4-chloro-5-({2-[4-(2,3-dihydro-benzo[1,4]dioxine-5-yl)-piperazine-1-yl]-ethyl}-methyl-amino)-2H-pyridazine-3-one, 20 cm³ of methanol and 0.8 g of a palladium charcoal catalyst (8% Pd, 28% C, 64% $H_2O$) are introduced. The reaction mixture is stirred at room temperature under a hydrogen pressure of 10 atm. for 2 hours. The hydrogen is released, the reaction mixture is filtered and the filtrate is evaporated. To the residue 10 cm³ of toluene are added and the mixture is distilled off in vacuo. The residue is suspended in 10 ml of diisopropyl ether. The crystals are filtered. The crude product is recrystallized from a 9:1 mixture of acetonitrile and water.

Thus, 0.62 g (73.8%) of the desired product are obtained. M.p.: 234–236° C.

Analysis: for $C_{19}H_{28}ClN_5O_4$ (425.92); calc.: C, 53.58%; H, 6.63%; Cl, 8.32%; N, 16.44%; found: C, 53.06%; H, 6.39%; Cl, 8.20%; N, 16.23%.

IR (KBr): 3389, 2414, 1653, 1600, 1473.

¹H-NMR (DMSO-$d_6$, i400): 12.23 (bs, 1H), 11.41 (b, 1H), 7.91 (d, J=2.7 Hz, 1H), 6.76 (~t, J=8.1 Hz, 1H), 6.58 (dd, J1=1.2 Hz, J2=8.2 Hz, 1H), 6.52 (dd, J1=1.2 Hz, J2=8.1 Hz, 1H), 6.64 (~s, 1H), 4.25 (m, 2H), 4.23 (m, 2H), 3.89 (m, 2H), 3.52 (m, 4H), 3.4–3.0 (m, 6H), 2.98 (s, 3H).

¹³C-NMR (DMSO-$d_6$, i400): 161.82, 149.04, 144.14, 139.98, 136.28, 128.75, 120.62, 112.11, 110.60, 98.22, 64.10, 63.90, 51.47, 51.16. 47.09, 45.21, 37.61.

Example 16

Preparation of 5-(2-(4-(2,3-dihydro-benzo[1,4]dioxine-5-yl)-piperazine-1-yl)-ethyl-methyl-amino)-2-methyl-2H-pyridazine-3-one-hydrochloride Into a pressure-proof hydrogenating apparatus 4.0 g (0.0095 mole) of 4-chloro-5-({2-[4-(2,3-dihydro-benzo[1,4]dioxine-5-yl)-piperazine-1-yl]-ethyl}-methyl-amino)-2-methyl-2H-pyridazine-3-one, 300 cm³ of methanol and 4.0 g of a palladium charcoal catalyst (8% Pd, 28% C, 64% $H_2O$) are weighed in. The reaction mixture is stirred at room temperature under a hydrogen pressure of 10 atm. for 3 hours. The hydrogen is released, the reaction mixture is filtered and the catalyst is washed 4 times with 50 cm³ of methanol each and the mother lye is evaporated. To the residue 30 ml of toluene are added and the solvent is distilled off in vacuo. The residue is suspended in diisopropyl ether, the precipitated crystals are filtered, the crude product is dissolved in a 9:1 mixture of acetonitrile and water under reflux, filtered and the filtrate is evaporated to half volume. The residual mother lye is cooled and stirred. The precipitated crystals are filtered.

Thus, 3.02 g (75.5%) of the desired product are obtained. M.p.: 249–251° C.

Analysis: for $C_{20}H_{28}ClN_5O_3$ (421.93); calc.: C, 56.93%; H, 6.69%; Cl, 8.40%; N, 16.60%; found: C, 56.55%; H, 6.39%; Cl, 8.72%; N, 16.8%.

IR (KBr): 2345, 1637, 1596, 1477, 1088.

¹H-NMR (DMSO-$d_6$, g200): 11.25 (b, 1H), 7.94 (d, J=2.7 Hz 1H), 6.77 (~t, J=8.1 Hz, 1H), 6.55 (m, 2H), 5.76 (d, J=2.7 Hz, 1H), 4.24 (s, 4H), 3.88 (m, 2H), 3.7–2.9 (m, 10H), 3.53 (s, 3H), 2.98 (s, 3H).

¹³C-NMR (DMSO-$d_6$, i400): 160.46, 148.76, 144.10, 139.89, 136.25, 128.15, 120.53, 112.02, 110.55, 98.13, 64.04, 63.84, 51.48, 47.03. 45.17, 37.52.

Example 17

Preparation of 4-chloro-5-({2-[4-(2,3-dihydro-benzo[1,4]dioxine-5-yl)-piperazine-1-yl]-ethyl}-methyl-amino)-2-methyl-2H-pyridazine-3-one 7.48 g (0.034 mole) of 1-(2,3-dihydro-benzo[1,4]dioxine-5-yl)-piperazine, 7.1 g (0.066 mole) of sodium carbonate, 1.13 g (0.0075 mole) of sodium iodide, 7.23 g (0.031 mole) of 5-(2-chloro-ethylamino)-4-chloro-2-methyl-2H-pyridazine-3-one and 42 cm³ of dimethyl formamide are admixed. The reaction mixture is stirred at 110° C. at 4 hours, whereupon 270 cm³ of water are added dropwise and the aqueous phase is extracted 3 times in 100 ml of ethylacetate each. The united organic phases are washed twice with 100 ml of water and twice with 50 ml of a saturated aqueous sodium chloride solution each, dried over magnesium sulfate and filtered. The organic phase is evaporated and the residue is suspended in a mixture of ethyl acetate and n-hexane. The crystals are filtered and dried. The crude product is recrystallized from 2-propanol.

Thus, 7.67 g (59.0%) of the desired compound are obtained. M.p.: 114–116° C.

Analysis: for $C_{20}H_{26}ClN_5O_3$ (419.91); calc.: C, 57.21%; H, 6.24%; Cl, 8.44%; N, 16.68%; found: C, 57.05%; H, 6.21%; Cl, 8.33%; N, 16.47%.

IR (Kr): 1642, 1591, 1473, 998.

$^1$H-NMR (DMSO-$d_6$, i400): 7.88 (s, 1H), 6.70, (~t, J=8.1 Hz, 1H), 6.48 (dd, J1=1.4 Hz, J2=8.2 Hz, 1H), 6.39 (dd, J1=1.4 Hz, J2=8.0 Hz, 1H), 4.21 (m, 2H), 4.20 (m, 2H), 3.59 (s, 3H), 3.59 (t, 2H), 3.06 (s, 3H), 2.82 (m, 4H), 2.56 (t, J=6.3 Hz, 2H), 2.50 (m).

$^{13}$C-NMR (DMSO-$d_6$, i400): 157.74, 148.29, 143.98, 141.68, 136.31, 131.45, 120.45, 111.19, 111.01, 110.21, 63.95, 63.85, 55.15, 53.05, 50.28. 50.03, 39.81 39.7.

Example 18

Preparation of 5-(2-{benzyl-[2-(2,3-dihydro-benzo[1,4]dioxine-5-yl-oxy)-ethyl]-amino}-ethyl-amino)-4-chloro-2-methyl-2H-pyridazine-3-one A mixture of 4.95 g (0.017 mole) of benzyl-[2-(2,3-dihydro-benzo[1,4]dioxine-5-yl-oxy)-ethyl]-amine, 4.68 g (0.044 mole) of sodium carbonate, 0.73 g (0.0047 mole) of sodium iodide, 4.68 g (0.021 mole) of 5-(2-chloro-ethyl-amino)-4-chloro-2-methyl-2H-pyridazine-3-one and 26 cm³ of dimethyl formamide are stirred at 110° C. for 5 hours. To the reaction mixture 200 cm³ of water are added dropwise and the aqueous phase is extracted 4 times with 100 cm³ of dichloro methane each. The united organic phases are washed successively twice with 100 cm³ of water each and twice with 50 cm³ of a saturated sodium chloride solution each, dried over magnesium sulfate and filtered. The organic phase is evaporated. The residue is purified by chromatography on a silica gel column and elution with a 79:1 mixture of chloroform and methanol.

Thus, 2.76 g (34.5%) of the desired compound are obtained. M.p: 78–80° C.

IR(KBr): 3381, 3364, 1613, 1113.

$^1$H-NMR (DMSO-$d_6$, i400): 7.39 (s, 1H), 7.33 (m, 2H), 7.28 (m, 2H), 7.23 (m, 1H), 6.73 (~t, J=8.3 Hz, 1H), 6.53 (dd, J1=1.4 Hz, J2=8.3 Hz, 1H), 6.42 (dd, J1=1.3 Hz, J2=8.2 Hz, 1H), 5. 55 (bt, 1H), 4.23 (m, 4H), 4.09 (t, J=5.5 Hz, 2H), 3.75 (s, 2H), 3.72 (s, 3H), 3.32 (~q, J=5.6 Hz, 2H), 3.02 (t, J=5.5 Hz, 2H), 2.88 (t, J=5.8 Hz, 2H).

$^{13}$C-NMR (DMSO-$d_6$, i400): 157.80, 148.00, 144.37, 143.98, 138.55, 133.55, 128.80, 128.49, 127.36, 125.47, 120.15, 10.40, 107.29, 105.32, 67.44, 64.36, 64.13, 59.65, 52.79, 52.64, 40.21, 40.08.

Example 19

Preparation of 5-{2-[2-(2,3-dihydro-benzo[1,4]dioxine-5-yl-oxy)-ethyl-amino]-ethyl-amino}-2-methyl-2H-pyridazine-3-one-hydrochloride Into a hydrogenating apparatus 1.75 g (0.0037 mole) of 5-(2-{benzyl-[2-(2,3-dihydro-benzo[1,4]dioxine-5-yl-oxy)-ethyl]-amino}-ethyl-amino)-4-chloro-2-methyl-2H-pyridazine-3-one, 50 cm³ of ethanol, 5 cm³ of water and 3.5 g of a palladium charcoal catalyst (8% Pd, 28% C, 64% $H_2O$) are introduced. To the reaction mixture at room temperature 6 cm³ of hydrazine hydrate are added dropwise and the temperature is raised to the boiling point. The reaction mixture is refluxed for half an hour, filtered off, the catalyst is washed 3 times with 30 cm³ of ethanol each and the mother lye is evaporated. To the residue twice 30 ml of toluene each are added and the mixture is evaporated in vacuo. From the residue salt is formed by using isopropanol containing hydrogen chloride.

Thus, 1.2 g (84.7%) of the desired compound are obtained. M.p.: 218–219° C.

IR (KBr): 3239, 2512, 1632, 1286, 1100.

$^1$H-NMR (DMSO-$d_6$, i400): 7.55 (d, J=2.8 Hz, 1H), 7.31 (bt, J=5.6 Hz, 1H), 6.81 (~t, J=8.2 Hz, 1H), 6.68 (dd, J1=1.5 Hz, J2=8.2 Hz, 1H), 6.58 (dd, J1=1.5 Hz, J2=8.2 Hz, 1H), 5.72 (d, J=2.7 Hz, 1H), 4.28 (m, 6H), 3.54 (s, 3H), 3.43 (~q, J=6.0 Hz, 2H), 3.34 (t, J=5.3 Hz, 2H), 3.16 (t, J=5.3 Hz, 2H).

$^{13}$C-NMR (DMSO-$d_6$, i400): 160.97, 148.77, 147.44, 144.34, 133.98, 130.85, 120.05, 110.70, 107.09, 95.07, 65.84, 64.00, 46.51, 45.65, 39.7, 38.26.

What we claim is:

1. Compounds of Formula

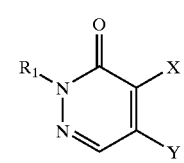

(I)

wherein $R_1$ is hydrogen or alkyl having 1–4 carbon atoms;

one of X and Y stands for hydrogen or halogen and the other represents a group of Formula

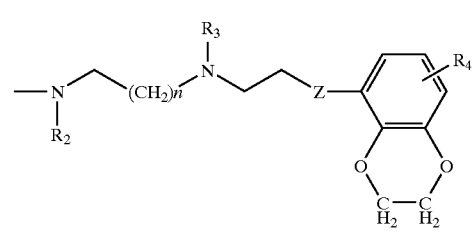

(II)

$R_2$ is hydrogen or alkyl having 1–4 carbon atoms;

n is 1, 2 or 3;

$R_3$ stands for hydrogen, alkyl having 1–4 carbon atoms or aryl-($C_{1-4}$ alkyl);

Z stands for oxygen; or $R_3$ and Z together with the groups placed between them form a piperazine ring; and $R_4$ stands for hydrogen, halogen, trifluoromethyl or alkoxy having 1–4 carbon atoms, and pharmaceutically acceptable acid addition salts thereof.

2. Compounds of Formula I according to claim 1, wherein $R_1$ is hydrogen or methyl;

one of X and Y stands for hydrogen or chlorine and the other represents a group of Formula II;

$R_2$ is hydrogen or methyl;

n is 1, 2 or 3;

R$_3$ stands for hydrogen;

Z stands for oxygen; or

R$_3$ and Z together with the groups placed between them form a piperazine ring; and R$_4$ stands for hydrogen or chlorine, and pharmaceutically acceptable acid addition salts thereof.

3. 5-chloro-4-{4-[4-(2,3-dihydrobenzo[1,4]dioxine-5-yl)-piperazine-1-yl]-butylamino}-2H-piridazin-3-one and pharmaceutically acceptable acid addition salts thereof.

4. 4-chloro-5-{2-[4-(2,3-dihydro-1,4-benzodioxine-5-yl)-piperazin-1-yl]-ethylamino}-2-methyl-2H-piridazin-3-one and pharmaceutically acceptable acid addition salts thereof.

5. 4-chloro-5-{2-[4-(2,3-dihydrobenzo[1,4]dioxine-5-yl)-piperazin-1-yl]ethyl}methylamino-2H-pyridazin-3-one and pharmaceutically acceptable acid addition salts thereof.

6. 4-{3-[2-(2,3-dihydrobenzo[1,4]dioxine-5-yloxy) ethylamino]-propylamino}-2H-pyridazine-3-one and pharmaceutically acceptable acid addition salts thereof.

7. 5-{2-[4-(2,3-dihydro-1,4-benzodioxine-5-yl)-piperazine-1-yl]-ethylamino}-2H-pyridazine-3-one and pharmaceutically acceptable acid addition salts thereof.

8. 5-{2-[4-(7-chloro-2,3-dihydrobenzo[1,4]dioxine-5-yl)-piperazine-1-yl]ethylamino}-2H-pyridazine-3-one and pharmaceutically acceptable acid addition salts thereof.

9. 5-{3-[4-(2,3-dihydro-1,4-benzodioxine-5-yl) piperazine-1-yl]-propylamino}-2H-pyridazine-3-one and pharmaceutically acceptable acid addition salts thereof.

10. 5-{2-[2-(2,3-dihydrobenzo[1,4]dioxine-5-yloxy) ethylamino)-ethylamino)-2H-pyridazine-3-one and pharmaceutically acceptable acid addition salts thereof.

11. 5-{2-[4-(2,3-dihydro1,4-benzodioxine-5-yl)-piperazine-1-yl]-ethylamino}-2-methyl-2H-pyridazine-3-one and pharmaceutically acceptable acid addition salts thereof.

12. 5-({2-[4-(2,3-dihydro-benzo[1,4]dioxine-5-yl)-piperazine-1-yl]-ethyl}-methyl-amino)-2H-pyridazine-3-one and pharmaceutically acceptable acid addition salts thereof.

13. 5-(2-(4-(2,3-dihydro-benzo[1,4]dioxine-5-yl)-piperazine-1-yl)-ethyl-methyl-amino)-2-methyl-2H-pyridazin-3-one and pharmaceutically acceptable acid addition salts thereof.

14. 4-chloro-5-({2-[4-(2,3-dihydro-benzo[1,4]dioxine-5-yl)-piperazine-1-yl]-ethyl}-methyl-amino)-2-methyl-2H-pyridazine-3-one and pharmaceutically acceptable acid addition salts thereof.

15. 5-{2-[2-(2,3-dihydro-benzo[1,4]dioxine-5-yl-oxy)-ethyl-amino]-ethyl-amino}-2-methyl-2H-pyridazine-3-one and pharmaceutically acceptable acid addition salts thereof.

16. Process for the preparation of compounds of Formula I wherein

R$_1$ is hydrogen or alkyl having 1–4 carbon atoms;

one of X and Y stands for hydrogen or halogen and the other represents a group of Formula II;

R$_2$ is hydrogen or alkyl having 1–4 carbon atoms;

n is 1, 2 or 3;

R$_3$ stands for hydrogen, alkyl having 1–4 carbon atoms or aryl-(C$_{1-4}$ alkyl);

Z stands for oxygen; or

R$_3$ and Z together with the groups placed between them form a piperazine ring; and R$_4$ stands for hydrogen, halogen, trifluoromethyl or alkoxy having 1–4 carbon atoms, and pharmaceutically acceptable acid addition salts thereof, which comprises:

a) for the preparation of compounds of Formula I, wherein X represents hydrogen or halogen, Y stands for a group of Formula II and R$_2$, R$_3$, R$_4$, Z and n are as stated above, reacting a compound of Formula

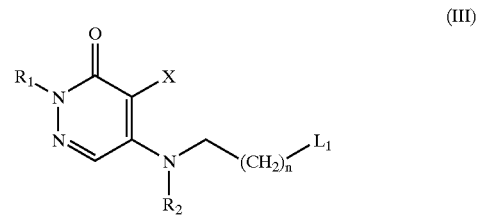
(III)

wherein L$_1$ represents a leaving group, and R$_1$, R$_2$, X and n are as stated above, with an amine of Formula

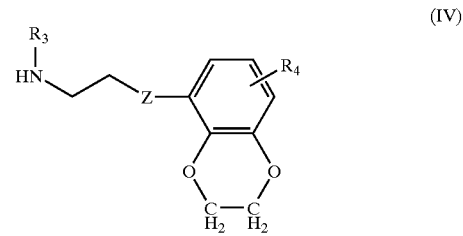
(IV)

wherein R$_3$, R$_4$ and Z are as stated above; or b) for the preparation of compounds of Formula I, wherein Y represents hydrogen or halogen, X stands for a group of Formula II and R$_2$, R$_3$, R$_4$, Z and n are as stated above, reacting a compound of Formula

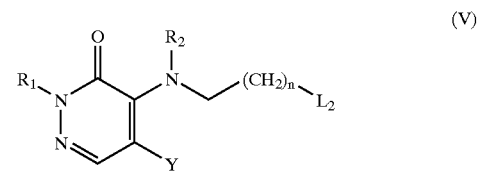
(V)

wherein L$_2$ is a leaving group, and R$_1$, R$_2$, Y and n are as stated above, with an amine of Formula IV wherein R$_3$, R$_4$ and Z are as stated above; or c) for the preparation of compounds of Formula I, wherein X represents hydrogen or halogen, Y stands for a group of Formula II and R$_2$, R$_3$, R$_4$, Z and n are as stated above, with the proviso that R$_3$ together with Z and the groups between them is other than a piperazine ring, reacting a compound of Formula

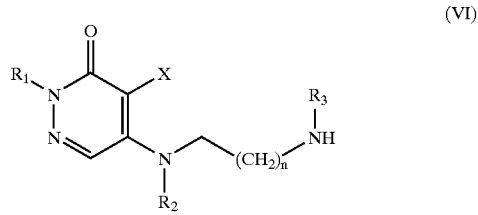
(VI)

VI, wherein R$_1$, R$_2$, R$_3$, X and n are as stated above, with a compound of Formula

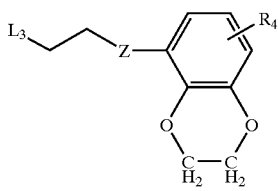

wherein $R_4$ and Z are as stated above and $L_3$ stands for a leaving group; or d) for the preparation of compounds of Formula I, wherein Y stands for hydrogen or halogen, X stands for a group of Formula II and $R_2$, $R_3$, $R_4$, Z and n are as stated above with the proviso that $R_3$ together with Z and the groups between them is other than a piperazine ring, reacting a compound of Formula

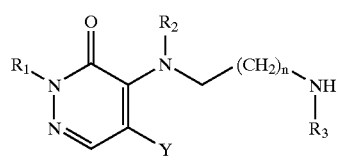

wherein $R_1$, $R_2$, $R_3$, Y and n are as stated above, with a compound of Formula VII, wherein Z and $R_4$ are as stated above and $L_3$ stands for a leaving group; or e) for the preparation of compounds of Formula I, wherein X represents halogen and Y stands for a group of Formula II and/or Y represents halogen and X stands for a group of Formula II and $R_1$, $R_2$, $R_3$, $R_4$, Z and n are as stated above, reacting a dihalopyridazinone derivative of Formula

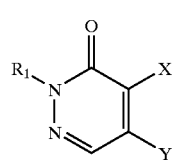

wherein $R_1$ is as stated above and X and Y independently from each other stand for halogen, with a compound of Formula

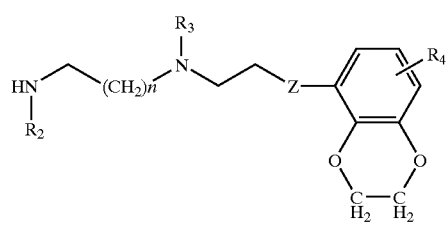

wherein $R_2$, $R_3$, $R_4$, Z and n are as stated above, and, if desired, subjecting an obtained substituted alkylaminopyridazinone derivative of Formula I, wherein X or Y stand for halogen, to catalytic dehalogenation to obtain a substituted alkylaminopyridazinone derivative of Formula I or its hydrochloride salt, wherein X represents hydrogen and Y stands for a group of Formula II or X represents a group of Formula II and Y stands for hydrogen; and/or converting a compound of Formula I into a pharmaceutically acceptable acid addition salt thereof or liberating a compound of Formula I from an acid addition salt thereof.

17. Pharmaceutical compositions comprising as active ingredient at least one compound of Formula I according to claim 1 or pharmaceutically acceptable acid addition salts thereof in admixture with suitable inert pharmaceutical carriers and/or auxiliary agents.

18. Pharmaceutical compositions according to claim 17 comprising as active ingredient 5-chloro-4-{4-[4-(2,3-dihydrobenzo[1,4]dioxine-5-yl)-piperazine-1-yl]-butylamino}-2H-piridazin-3-one;

4-chloro-5-{2-[4-(2,3-dihydro-1,4-benzodioxine-5-yl)-piperazine-1-yl]-ethylamino}-2-methyl-2H-piridazin-3-one;

4-chloro-5-{2-[4-(2,3-dihydrobenzo[1,4]dioxine-5-yl)-piperazine-1-yl]ethyl}methylamino-2H-pyridazin-3-one;

4-{3-[2-(2,3-dihydrobenzo[1,4]dioxine-5-yloxy)ethylamino]-propylamino}-2H-pyridazine-3-one;

5-{2-[4-(2,3-dihydro-1,4-benzodioxine-5-yl)-piperazine-1-yl]-ethylamino}-2H-pyridazine-3-one;

5-{2-[4-(7-chloro-2,3-dihydrobenzo[1,4]dioxine-5-yl)-piperazine-1-yl]ethylamino}-2H-pyridazine-3-one;

5-{3-[4-(2,3-dihydro-1,4-benzodioxine-5-yl)piperazine-1-yl]-propylamino}-2H-pyridazine-3-one;

5-{2-[2-(2,3-dihydrobenzo[1,4]dioxine-5-yloxy)ethylamino)-ethylamino)-2H-pyridazine-3-one;

5-{2-[4-(2,3-dihydro1,4-benzodioxine-5-yl)-piperazine-1-yl]-ethylamino}-2-methyl-2H-pyridazine-3-one;

5-(-{2-[4-(2,3-dihydro-benzo[1,4]-benzodioxine-5-yl)-piperazine-1-yl]-ethyl}-methyl-amino)-2H-pyridazine-3-one;

5-(2-(4-(2,3-dihydro-benzo[1,4]dioxine-5-yl)-piperazine-1-yl)-ethyl-methyl-amino)-2-methyl-2H-pyridazine-3-one;

4-chloro-5-({2-[4-(2,3-dihydro-benzo[1,4]dioxine-5-yl)-piperazine-1-yl]-ethyl}-methyl-amino)-2-methyl-2H-pyridazine-3-one;

5-{2-[2-(2,3-dihydro-benzo[1,4]dioxine-5-yl-oxy)-ethyl-amino]-ethyl-amino}-2-methyl-2H-pyridazine-3-one;

and pharmaceutically acceptable acid addition salts thereof.

19. Process for the preparation of pharmaceutical compositions according to claim 17 which comprises admixing at least one compound of Formula I or a pharmaceutically acceptable acid addition salt thereof with suitable inert pharmaceutical carriers and/or auxiliary agents.

20. Method of treatment of anxiolytic conditions and cognitive disorders which comprises administering to a person in need of such treatment a pharmaceutically effective amount of a compound of Formula I according to claim 1 or a pharmaceutically acceptable acid addition salt thereof.

* * * * *